United States Patent
Matwiejuk et al.

(10) Patent No.: US 9,834,574 B2
(45) Date of Patent: Dec. 5, 2017

(54) CRYSTALLINE 3-O-FUCOSYLLACTOSE

(71) Applicant: Glycom A/S, Hørsholm (DK)

(72) Inventors: Martin Matwiejuk, Hamburg (DE); Gyula Dekany, Sinnamon Park (AU)

(73) Assignee: GLYCOM A/S, Hørsholm (DK)

(*) Notice: Subject to any disclaimer, the term of this patent is extended or adjusted under 35 U.S.C. 154(b) by 25 days.

(21) Appl. No.: 14/442,017

(22) PCT Filed: Sep. 19, 2013

(86) PCT No.: PCT/DK2013/050300
§ 371 (c)(1),
(2) Date: May 11, 2015

(87) PCT Pub. No.: WO2014/075680
PCT Pub. Date: May 22, 2014

(65) Prior Publication Data
US 2015/0291642 A1  Oct. 15, 2015

(30) Foreign Application Priority Data

Nov. 13, 2012  (DK) .................................. 2012 70696

(51) Int. Cl.
*C07H 3/06* (2006.01)
*C07H 1/06* (2006.01)
*A23L 33/10* (2016.01)
*A23L 33/00* (2016.01)

(52) U.S. Cl.
CPC ................ *C07H 3/06* (2013.01); *A23L 33/10* (2016.08); *A23L 33/40* (2016.08); *C07H 1/06* (2013.01); *A23V 2002/00* (2013.01)

(58) Field of Classification Search
CPC .. C07H 3/06; C07H 1/06; A23L 33/40; A23L 33/10
See application file for complete search history.

(56) References Cited

FOREIGN PATENT DOCUMENTS

| CH | EP 2455387 A1 * | 5/2012 | ............ A23L 1/296 |
|---|---|---|---|
| WO | WO9310796 | 6/1993 | |
| WO | WO2010070104 | 6/2010 | |
| WO | WO2010115934 | 10/2010 | |
| WO | WO2010115935 | 10/2010 | |
| WO | WO2011150939 | 12/2011 | |
| WO | WO2012007585 | 1/2012 | |
| WO | WO2012112777 | 8/2012 | |
| WO | WO2013139344 | 9/2013 | |

OTHER PUBLICATIONS

Dumon, Cl. et al, "Assessment of the two heliobacter pylori alpha-1,3-fucosyltransferase ortholog genes for the large-scale synthesis of the LewisX human milk oligosaccharides by metabolically engineered *Escherichia coli*", Biotechnol. Prog., vol. 20, pp. 412-419, (2004).
Fernandez-Mayoralas, A. et al, "Synethesis of 3- and 2'-fucosyllactose and 3,2'-difucosyl-lactose from partially benzylated lactose derivatives", Carbohydrate Research, vol. 154, pp. 93-101, (1986).
Pereira, C. et al, "Synthesis of human milk oligosaccharides: 2'- and 3'-fucosyllactose", Heterocycles, 84:1:637-655, (2012).

* cited by examiner

*Primary Examiner* — Jonathan S Lau
(74) *Attorney, Agent, or Firm* — Neal, Gerber & Eisenberg LLP

(57) ABSTRACT

Crystalline 3-O-fucosyllactose, useful in a pharmaceutical composition and a nutritional formulation, is disclosed.

17 Claims, 2 Drawing Sheets

CRYSTALLINE 3-O-FUCOSYLLACTOSE

CROSS REFERENCE TO RELATED APPLICATIONS

This is a national stage filing in accordance with 35 U.S.C. §371 of PCT/DK2013/050300, filed Sep. 19, 2013, which claims the benefit of the priority of Denmark Patent Application No. PA 2012 70696, filed Nov. 13, 2012, the contents of each are incorporated herein by reference.

FIELD OF THE INVENTION

The present invention provides the trisaccharide 3-O-fucosyllactose (3-FL) in crystalline form, a method of making it and formulations containing it.

BACKGROUND OF THE INVENTION

In recent years, efforts have increasingly been made to produce industrially complex carbohydrates, such as secreted oligosaccharides. This has been due to the roles of such compounds in numerous biological processes in living organisms. Secreted oligosaccharides, such as human milk oligosaccharides ("HMOs"), have become particularly important commercial targets for nutrition and therapeutic applications. However, the synthesis and purification of these oligosaccharides have remained a challenging task. One of the simplest important human milk oligosaccharides is 3-O-fucosyllactose β-D-galactopyranosyl-(1→4)-(α-L-fucopyranosyl-(1→3))-D-glucose ("3-FL"):

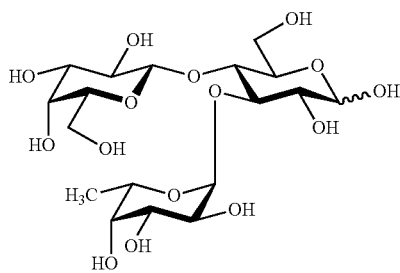

Several biological activities of 3-FL have been reported including its prebiotic, antibacterial, antiviral, immune system-enhancing and brain development-enhancing activities. These activities of 3-FL have made it a potentially attractive additive for nutritional and therapeutic products. However, it has been difficult to obtain 3-FL in pure form except at very high cost.

3-FL has been isolated from human milk by very costly and complicated chromatographic procedures. 3-FL synthesized by enzymatic, biotechnological and chemical processes (Dumon et al. *Biotechnol. Prog.* 20, 412 [2004], Fernandez-Mayoralas et al. *Carbohydrate Res.* 154, 93 [1986], and Pereira et al. *Heterocycles* 84, 637 [2012]) has been isolated as an amorphous material and thus it has been very costly to purify. This has made previous methods of making 3-FL too costly for commercialization.

Crystallization or recrystallization is one of the simplest and cheapest methods to separate a chemical product from contaminants and obtain it in pure form. In addition, crystalline modifications (polymorphs) of a solid compound is an important factor in its product development, because different crystalline forms affect the compound's properties—for example its thermodynamic stability, solubility, density, hygroscopicity, electrical properties (such as dielectric constant, conductivity), mechanical properties (such as friability, hardness, breaking strength, elasticity), optical properties (such as colour, transparency, refraction), etc.—diversely.

For this reason, ways have been sought for obtaining crystalline 3-FL.

SUMMARY OF THE INVENTION

The present invention provides a crystalline 3-FL and a method for making it that is believed suitable for its large scale purification. Thus, the crystalline product of this invention is a high purity 3-FL that is suitable for nutritional and pharmaceutical products.

Accordingly, crystalline 3-FL can be obtained when 3-FL in syrupy form is dried under high vacuum for prolonged time. Additionally, amorphous/precipitated 3-FL can be converted to crystalline material when suspended and stirred in bad solvent(s) for some time. Moreover, having obtained crystalline sample, it can be used as seeding crystals for classical crystallization from solvent system, preferably those comprising an alcoholic solvent, more preferably an alcoholic solvent and water.

BRIEF DESCRIPTION OF THE FIGURES

The invention will be described in further detail hereinafter with reference to the accompanying figures, in which.

DETAILED DESCRIPTION OF THE INVENTION

Figure 1:
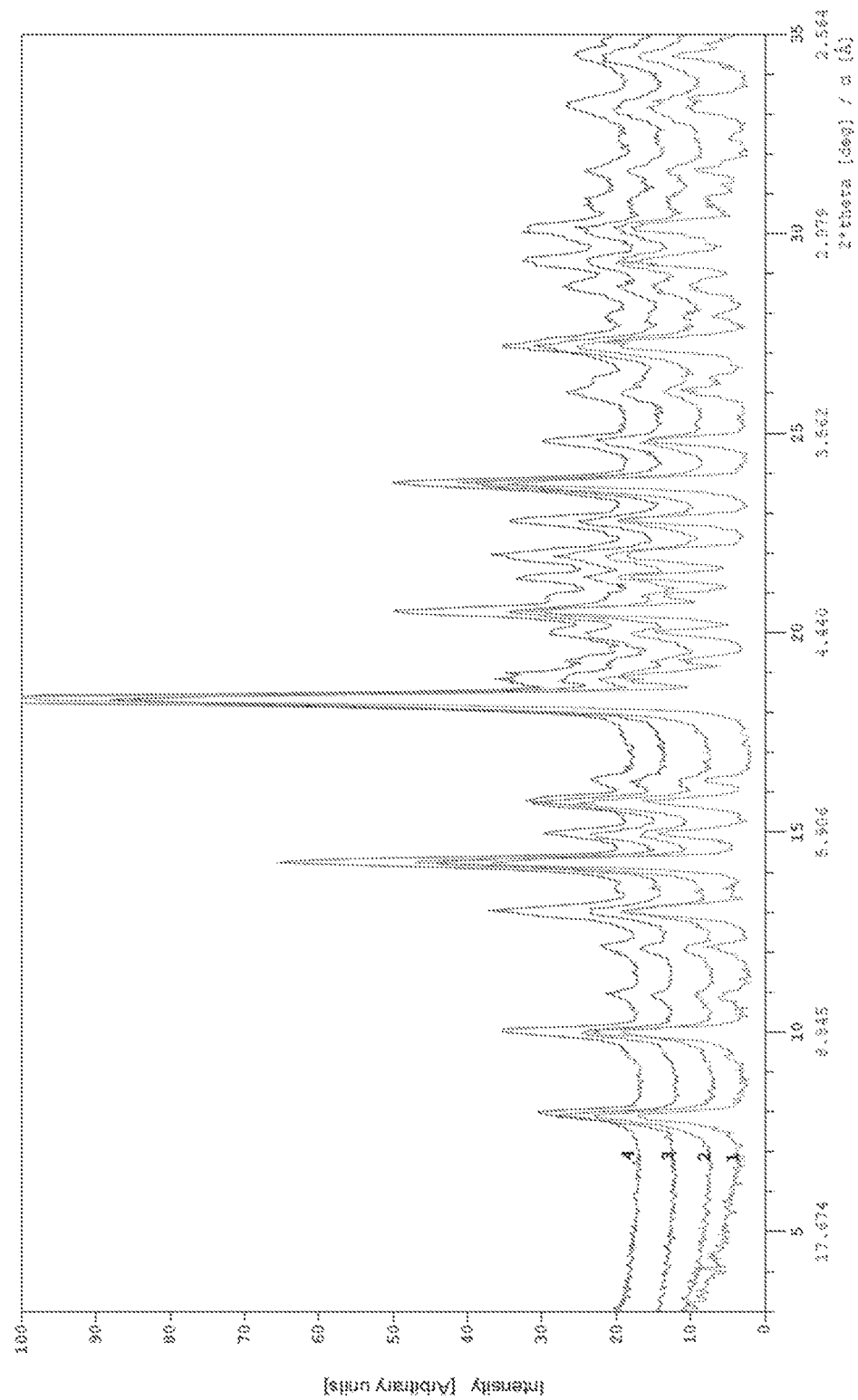
FIG. 1 shows comparison of the X-ray powder diffraction patterns of crystalline 3-O-fucosyllactose samples obtained according to examples 6-9 (1: example 6; 2: example 9; 3: example 7; 4: example 6).

This invention provides a crystalline 3-FL that can be obtained as polycrystalline material. The crystalline 3-FL comprises X-ray powder diffraction reflections, based on a measurement using CuKa radiation, at 18.36±0.20 2Θ, more preferably at 18.36±0.20 2Θ and 14.26±0.20 2Θ, even more preferably at 18.36±0.20 2Θ, 14.26±0.20 2Θ and 23.75±0.20 2Θ, and most preferably at 18.36±0.20 2Θ, 14.26±0.20 2Θ, 23.75±0.20 2Θ and 9.99±0.20 2Θ. The XRPD pattern is shown in FIG. 1 and the list of peaks of the XRPD pattern of the crystalline 3-FL is set forth in Table 1, below.

TABLE 1

| 2Θ | rel. | 2Θ | rel. intensity |
|---|---|---|---|
| 7.92 | 12.78 | 24.81 | 12.35 |
| 9.36 | 2.33 | 25.40 | 1.35 |
| 9.99 | 19.07 | 26.07 | 8.02 |
| 10.84 | 3.47 | 26.39 | 4.88 |
| 12.16 | 4.5 | 27.16 | 16.14 |
| 13.03 | 15.28 | 27.26 | 16.74 |
| 13.60 | 2.22 | 27.94 | 4.33 |
| 14.26 | 41.44 | 28.71 | 7.42 |
| 14.97 | 11 | 29.32 | 14.63 |
| 15.77 | 12.62 | 30.12 | 14.68 |
| 16.31 | 5.42 | 30.80 | 5.25 |
| 18.36 | 100 | 31.20 | 3.14 |
| 18.92 | 15.55 | 31.59 | 6.88 |

TABLE 1-continued

| 2Θ | rel. | 2Θ | rel. intensity |
|---|---|---|---|
| 19.28 | 8.02 | 31.76 | 3.63 |
| 20.01 | 11.76 | 32.41 | 2.38 |
| 20.55 | 27.95 | 33.16 | 7.58 |
| 20.96 | 10.67 | 33.40 | 7.69 |
| 21.40 | 15.22 | 34.20 | 2.93 |
| 21.96 | 15.28 | 34.44 | 9.32 |
| 22.83 | 15.71 | 34.76 | 4.98 |
| 23.75 | 35.48 | | |

The novel crystalline of 3-FL can be considered as an anomeric mixture of α- and β-anomers or even pure form of one of the anomers.

Figure 2:
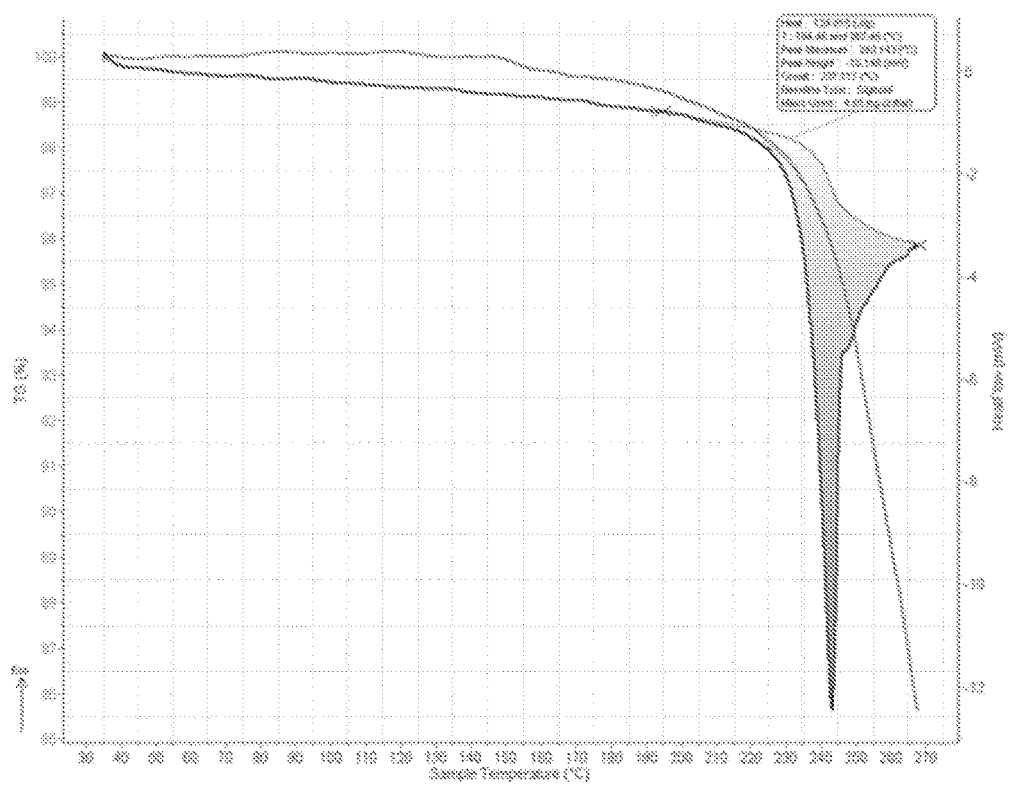
FIG. 2 shows the DSC thermogram of crystalline 3-O-fucosyllactose.

Crystalline 3-O-fucosyllactose displays, in DSC investigations, an endothermic reaction with a peak maximum at 243±5° C., more preferably at 243±4° C., even more preferably at 243±3° C., most preferably at 243±2° C., in particular at 243±1° C. (see FIG. 2).

Preferably, the crystalline 3-FL is substantially free from organic solvents and/or water. The term "substantially free from organic solvents and/or water" preferably means herein that the content of any organic solvent(s) and/or water is at most 1000 ppm, preferably at most 800 ppm, more preferably at most 600 ppm, most preferably at most 400 ppm and in particular at most 200 ppm.

Also preferably, the crystalline 3-FL is substantially pure. The term "substantially pure" preferably means herein that the crystalline 3-FL contains less than 10 w/w % of impurity, preferably less than 5 w/w % of impurity, more preferably less than 1 w/w % of impurity, most preferably less than 0.5 w/w % of impurity, in particular less than 0.1 w/w % of impurity. The term "impurity" preferably means herein any physical entity different from the crystalline 3-FL, such as an amorphous 3-FL, unreacted intermediate(s) remaining from the synthesis of 3-FL, by-product(s), degradation product(s), inorganic salt(s) and/or other contaminations different to organic solvent(s) and/or water.

The crystalline 3-FL can be obtained when solid, preferably amorphous or only partially crystalline 3-FL suspended in an antisolvent (solvent in which 3-FL is practically insoluble or has limited solubility) is stirred. The antisolvent is preferably a $C_1$-$C_6$ alcohol, more preferably methanol, ethanol, n-propanol, i-propanol, n-butanol, i-butanol, s-butanol or t-butanol, particularly preferably methanol or isopropanol. To convert the amorphous material to crystals, a prolonged and, preferably, vigorous agitation is required, at least 4-6, preferably 10-12, more preferably 18-20 hours at room temperature. It is possible to heat the antisolvent up to 50-60° C. which reduces the crystallization time to about 1-3 hours.

In addition, syrupy or oily 3-O-fucosyllactose can be solidified and crystallized by keeping it for a prolonged period, preferably at least 4-6, more preferably 10-12, particularly 16-18 hours under high vacuum, preferably about 30 mbar or less, more preferably about 15 mbar or less, particularly about 5 mbar or less, e.g. with an oil pump.

This invention also provides a process for preparing the crystalline 3-FL by crystallization from a solvent system in the presence of seed crystals. The solvent system preferably comprises one or more $C_1$-$C_6$ alcohols preferably mixed with water. The term "$C_1$-$C_6$ alcohol" preferably means a hydroxy- or dihydroxy-alkane having 1 to 6 carbon atoms, such as methanol, ethanol, n-propanol, i-propanol, n-butanol, i-butanol, s-butanol, t-butanol, amylalcohol, n-hexanol, ethylene glycol or propylene glycol. Preferred $C_1$-$C_6$ alcohols are selected from the group of methanol, ethanol, n-propanol, i-propanol, n-butanol, i-butanol, s-butanol and t-butanol. The preferred solvent system comprises methanol, ethanol, n-propanol, i-propanol or mixtures thereof, in particular methanol or isopropanol, and water.

Amorphous or syrupy 3-FL to be crystallized can be made by known methods but preferably via the procedure depicted in Scheme 1 below. In this regard, a thiophenyl fucosyl donor (WO 2011/115934) and a lactose derivative acceptor (WO 93/10796) can be coupled to a fully protected 3-FL derivative which has been deprotected successively by Zemplén deacylation, acid treatment and catalytic hydrogenolysis to produce 3-FL.

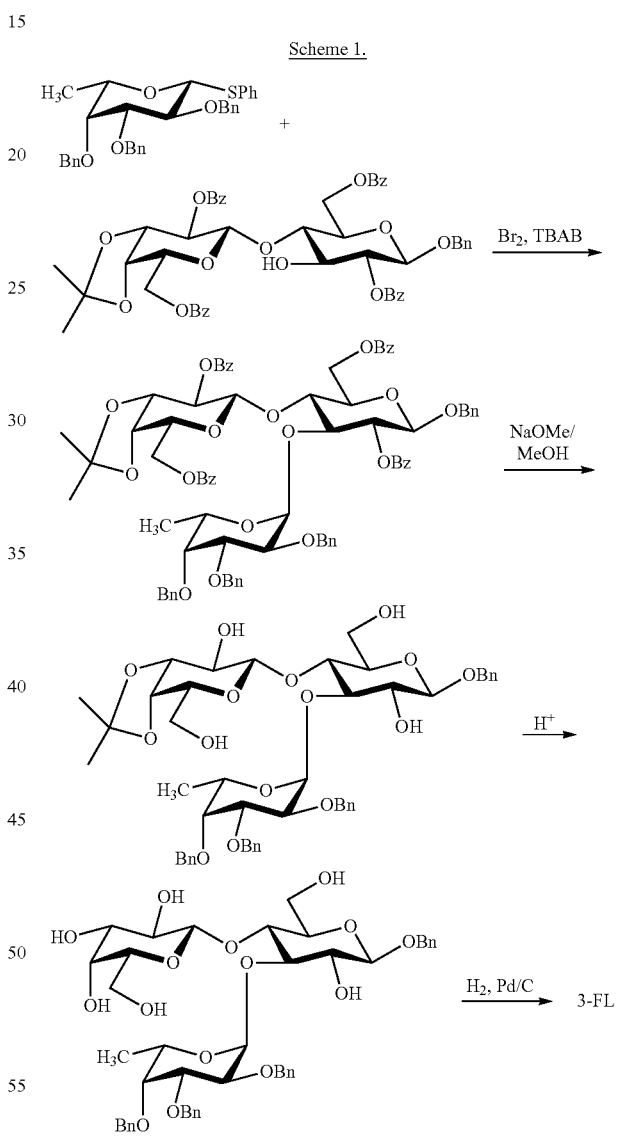

Scheme 1.

The crystalline 3-FL of this invention is suitable for use as a pharmaceutical agent. Pharmaceutical compositions for such use can contain the crystalline 3-FL as an active ingredient and one or more conventional pharmaceutically acceptable carriers, as well as additives, adjuvants, excipients and diluents (water, gelatine, talc, sugars, starch, gum arabic, vegetable gums, vegetable oils, polyalkylene glycols, flavouring agents, preservatives, stabilizers, emulsifying agents, lubricants, colorants, fillers, wetting agents, etc.) as described in the standard reference text, Remington's Pharmaceutical Sciences. The amounts of such ingredients can vary depending on whether the pharmaceutical compositions are intended for use with infants, children or adults or subjects having specialized needs.

The crystalline 3-FL of this invention is suitable also for nutritional use. Nutritional formulations, such as foods, drinks or feeds, for such use can contain the crystalline 3-FL as an active ingredient, together with other edible micronutrients, vitamins and minerals. The amounts of such ingredients can vary depending on whether the nutritional formulations are intended for use with normal, healthy infants, children, adults or subjects having specialized needs (e.g. suffering from metabolic disorders). Micronutrients include, for example, edible oils, fats or fatty acids (such as coconut oil, soy-bean oil, monoglycerides, diglycerides, palm olein, sunflower oil, fish oil, linoleic acid, linolenic acid etc.), carbohydrates (such as glucose, fructose, sucrose, maltodextrin, starch, hydrolysed cornstarch, etc.) and proteins from casein, soy-bean, whey or skim milk, or hydrolysates of these proteins, but protein from other sources (either intact or hydrolysed) can be used as well. Vitamins A, B1, B2, B5, B6, B12, C, D, E, H, K, folic acid, inositol and nicotinic acid and minerals and trace elements, such as Ca, P, K, Na, Cl, Mg, Mn, Fe, Cu, Zn, Se, Cr and I, can also be used.

A preferred nutritional formulation containing the crystalline 3-FL of this invention is an infant formula, i.e., a foodstuff intended for use by infants during their first 4-6 months of life and satisfying by itself their nutritional requirements. The infant formula can contain one or more probiotic *Bifidobacterium* species, prebiotics such as fructooligosaccharides and galactooligosaccharides, proteins from casein, soy-bean, whey or skim milk, carbohydrates such as lactose, saccharose, maltodextrin, starch or mixtures thereof, lipids (e.g. palm olein, sunflower oil, safflower oil) and vitamins and minerals essential in a daily diet. The infant formula preferably contains 0.1-3.0 g of the crystalline 3-FL/100 g of the infant formula.

The crystalline 3-FL of this invention can also be used as a food supplement. The food supplement can also contain other active ingredients, such as one or more probiotics, vitamins, minerals, trace elements and other micronutrients. The food supplement can be for example in the form of tablets, capsules, pastilles or a liquid and contain conventional additives such as binders, coatings, emulsifiers, solubilising agents, encapsulating agents, film forming agents, adsorbents, carriers, fillers, dispersing agents, wetting agents, jellifying agents and gel forming agents. The daily dose of 3-FL can range from 0.1 to 3.0 g.

The crystalline 3-FL of this invention is further suitable for use as an active ingredient in the preparation of nutritional formulations including foods, drinks and feeds, preferably infant formulas, and food supplements. The nutritional formulations can be prepared in a conventional manner, for example by admixing micronutrient components in appropriate proportions, then adding vitamins and minerals. To avoid thermal degradation or decomposition, heat sensitive vitamins can be added after homogenization. Lipophilic vitamins can be dissolved in a fat source before mixing. A liquid mixture can made with water, the temperature of which is preferably about 50-80° C. to help dissolution or dispersal of the ingredients. The crystalline 3-FL polymorph can then be added. The resulting mixture can then be homogenized by flash heating to about 80-150° C. by steam injection, heat exchanger or autoclave. This thermal treatment also reduces significantly the bacterial loads. The hot mixture can then be cooled rapidly to about 60-80° C. If needed, further homogenization can be carried out at this temperature under high pressure of about 2-30 MPa. After cooling, heat sensitive constituents can then be added, and the pH and the content of the solids can be conveniently adjusted. The resulting mixture is then dried to a powder by, for example, conventional spray drying or freeze drying methods. Probiotics can then be added by dry-mixing.

Other features of the invention will become apparent from the following examples which illustrate the invention but do not limit it.

EXAMPLES

Example 1. Benzyl 3',4'-O-isopropylidene-2,6,2',6'-tetra-O-benzoyl-β-lactoside Benzyl 3',4'-O-isopropylidene-β-lactoside (20 g) was dissolved in pyridine (30 ml). The solution was cooled to 0° C. and a mixture of benzoyl chloride (21 ml) and DCM (40 ml) was added dropwise through a dropping funnel over 6 h. The reaction mixture was stirred for another 2 h at 0° C. and at 5° C. for 24 hours. Methanol (10 ml) was then added and the solvents were removed in vacuo. The remaining residue was redissolved in EtOAc (200 ml) and washed with water (100 ml), sat. NaHCO$_3$ (100 ml), 2×1M HCl (100 ml), water (100 ml) and brine (100 ml). After removing the solvent in vacuo, the residue was recrystallized from MeOH (28 g, 72%).

Example 2. Benzyl 3-O-(2,3,4-tri-O-benzyl-α-L-fucopyranosyl)-3',4'-O-isopropylidene-2,6,2',6'-tetra-O-benzoyl-β-lactoside To a solution of phenyl 2,3,4-tri-O-benzyl-1-thio-β-L-fucopyranoside (133 g) in DCM (439 ml) bromine (16 ml) in DCM (50 ml) was added dropwise at 0° C. over a period of 60 minutes. After addition of the bromine solution the reaction mixture was stirred for additional 15 to 20 minutes. Cyclohexene (35 ml) was then added dropwise, followed by the addition of the product of Example 1 (120 g) and TBAB (8 g) in DCM (330 ml) and DMF (330 ml). The reaction mixture was stirred until TLC (Toluene/Acetone 12:1) showed completion, then it was diluted with 1.7 l of EtOAc. The organic layer was washed with sat. Na$_2$S$_2$O$_3$/sat. NaHCO$_3$ (1:1), sat. NaHCO$_3$/brine (4:1), water/brine, water/brine/1N HCl (1:1:1), sat. NaHCO$_3$/brine (2:1), and brine. The organic phase was dried over MgSO$_4$ and the solvents were removed in vacuo to obtain an orange oil which was recrystallized from EtOAc/Hexane (1:3) to obtain 148 g of crystals (84%).

Example 3. Benzyl 3-O-(2,3,4-tri-O-benzyl-α-L-fucopyranosyl)-3',4'-O-isopropylidene-β-lactoside The product of example 2 (148 g) was added to a 0.1 M solution of NaOMe in methanol (1.5 l). The suspension was warmed to 40° C. Complete debenzoylation was confirmed by TLC (toluene/acetone 1:1). H$^+$-IR120 Amberlite resin was added to neutralize the solution and the methanol was removed in vacuo. The residue was redissolved in EtOAc (1350 ml) and extracted with water (900 ml) 0.5 N HCl (900 ml), sat. NaHCO$_3$ (900 ml) and brine (450 ml). The solvent was removed in vacuo and the product was crystallised from EtOAc/hexane (1:2) to yield 79 g of product (79%). M.p.: 101-103° C.

Example 4. Benzyl 3-O-(2,3,4-tri-O-benzyl-α-L-fucopyranosyl)-β-lactoside

The product of example 3 (79 g) was dissolved in DCM (400 ml), MeOH (280 ml) and water (40 ml). TFA (80 ml)

was then added slowly at room temperature. After the addition is completed, the temperature was raised to 40° C. The progress of the reaction was followed by TLC (toluene/acetone 1:2). When no starting material could be detected, the reaction was cooled down in an ice-bath to 0° C. Slowly and portionwise 500 ml of sat. NaHCO$_3$ solution was added followed by EtOAc (1.2 l) together with additional 250 ml of sat. NaHCO$_3$ solution and 250 ml of brine. The organic layer was extracted two more times with 500 ml of sat. NaHCO$_3$ solution and 500 ml of brine. The solvent was removed in vacuo and the residue was crystallised from EtOAc/Et$_2$O (2:3) to yield 60 g of product (80%). $^1$H-NMR (CD$_3$OD) δ (ppm): 1.18 (d, 3=6.1 Hz, 3H); 3.34-3.56 (m, 4H); 3.57-3.69 (m, 2H); 3.78 (m, 2H); 3.95 (m, 7H); 4.1 (dd, 3=2.9 Hz, J=10.1 Hz, 1H); 4.4 (d, 3=7.6 Hz, 1H); 4.44 (d, 3=7 Hz, 1H); 4.57 (d, 3=11.0 Hz, 1H); 4.65 (d, H=11.7 Hz, 1H); 4.69 (d, 11.7 Hz, 1H); 4.81 (m, 1H); 4.93 (m, 3H); 5.7 (d, J=3.96 Hz, 1H); 7.15-7.57 (m, 20H). $^{13}$C-NMR (CD$_3$OD) δ (ppm): 15.75, 60.17, 60.18, 62.34, 66.43, 69.00, 70.77, 71.78, 71.93, 72.82, 73.65, 75.25, 75.55, 75.93, 76.14, 76.28, 77.57, 78.90, 78.94, 78.97, 97.09, 102.38, 102.58, 127.22, 127.28, 127.32, 127.37, 127.51, 127.62, 127.98, 128.07, 128.11, 128.12, 128.16, 128.45, 137.78, 138.50, 139.11, 139.42. M.p.: 123-125° C.

Example 5. 3-O-Fucosyllactose

The product of Example 4 (3.8 g) was dissolved in a mixture of isopropanol-methanol (1:2, 60 ml). 10% Pd on charcoal (0.23 g) was added and the mixture was stirred under H$_2$-atmosphere (20 bar in an autoclave) at 40° C. for 24 hours. The precipitated product was dissolved by adding small amount of water and few drops of acetic acid, and the hydrogenolysis was continued for 8 hours. The catalyst was filtered off and the solvents were removed. The product was dried in vacuo and precipitated by adding propanol (practically quantitative yield) giving an amorphous powder. $^1$H-NMR (D$_2$O) δ (ppm): 1.0 (d, J=7 Hz, 3H); 3.23-3.34 (m, 2H); 3.35-3.51 (m, 3H); 3.52-3.74 (m, 9H); 3.74-3.83 (m, 2H); 4.24 (d, J=7.9 Hz, 1H); 4.46 (d, J=7.9 Hz, 0.52H); 5.00 (d, J=3.7 Hz, 0.43H); 5.19 (d, J=4 Hz, 0.43H); 5.25 (d, J=4.1 Hz, 0.57H). $^{13}$C-NMR (D$_2$O) δ (ppm): 15.34, 59.78, 59.87, 61.62, 61.66, 66.57, 66.61, 68.13, 68.16, 68.43, 69.32, 69.38, 71.01, 71.24, 72.06, 72.50, 72.69, 72.75, 72.78, 74.80, 75.06, 75.47, 75.63, 77.09, 92.19, 95.92, 98.48, 98.61, 101.90. HPLC purity: 95-98%.

Example 6. Crystallization

The procedure according to Example 5 was repeated—except after removal of the solvents, the resulting syrupy or oily product was kept under high vacuum (5 mbar) for 18 hours at room temperature, and the 3-O-fucosyllactose product was obtained as crystalline material.

Example 7. Crystallization

Amorphous 3-FL according to Example 5 (1.0 g) was suspended in methanol (10 ml) and stirred at room temperature for overnight. The solid was then filtered off, washed with cold methanol and dried to get crystalline 3-FL (614 mg).

Example 8. Crystallization

Amorphous 3-FL according to Example 5 (1.5 g) was suspended in methanol (6 ml) and heated at 60° C. for 3 hours. After cooling down the solid was filtered off, washed with cold methanol and dried to get crystalline 3-FL (778 mg).

Example 9. Crystallization

Amorphous 3-FL according to Example 5 (2.76 g) was suspended in methanol (4 ml) and heated to 50-60° C. Water was then added until a clear solution was obtained at the same temperature. The solution was allowed to start cooling down, seeding crystals (obtained according to any one of Examples 6 to 8) were added and while the seeded solution was cooling down, 6 portions of methanol (2 ml each) were added successively. The solid formed was then filtered off, washed with cold methanol and dried to get crystalline 3-FL (1.31 g).

Example 10. X-Ray Powder Diffraction

XRPD investigation was conducted with a Philips PW 1830/PW1050 instrument in transmission geometry, using CuKα radiation made monochromatic by means of a graphite monochromator. D-spacings were calculated from the 2Θ values, based on a wavelength of 1.54186 Å. As a general rule the 2Θ values have an error rate of ±0.2 Å. FIG. 1 clearly shows that the X-ray powder diffraction patterns of the crystalline 3-FL samples obtained in Examples 6-9 are identical.

Example 11. DSC Analysis

The measurement was carried out on a SETARAM Labsys Evo TG-DSC thermoanalyzer, in flowing high purity (6.0) helium atmosphere (flow rate 30 mV/min) in the temperature range of 30-300° C. with a constant heating rate of 10 K/min, using standard 100 μl platinum crucible. Sample amount was 4.65 mg.

The invention claimed is:

1. Crystalline 3-O-fucosyllactose, wherein the crystalline 3-O-fucosyllactose displays X-ray powder diffraction reflections, based on a measurement using CuKa radiation, at 18.36±0.20 2Θ and 14.26±0.20 2Θ.

2. The crystalline 3-O-fucosyllactose of claim 1, wherein the crystalline 3-O-fucosyllactose displays, in DSC investigations, an endothermic reaction with peak temperature at 243±5° C.

3. The crystalline 3-O-fucosyllactose of claim 1, wherein the crystalline 3-O-fucosyllactose is substantially pure.

4. The crystalline 3-O-fucosyllactose of claim 1, wherein the crystalline 3-O-fucosyllactose is substantially free from organic solvent and/or water.

5. The crystalline 3-O-fucosyllactose of claim 1, wherein the crystalline 3-O-fucosyllactose displays X-ray powder diffraction reflections, based on a measurement using CuKa radiation, at 18.36±0.20 2Θ, 14.26±0.20 2Θ and 23.75±0.20 2Θ.

6. The crystalline 3-O-fucosyllactose of claim 1, wherein the crystalline 3-O-fucosyllactose displays X-ray powder diffraction reflections, based on a measurement using CuKa radiation, at 18.36±0.20 2Θ, 14.26±0.20 2Θ, 23.75±0.20 2Θ and 9.99±0.20 2Θ.

7. The crystalline 3-O-fucosyllactose of claim 1, wherein the 3-O-fucosyllactose displays, in DSC investigations, an endothermic reaction with peak temperature at 243±4° C.

8. The crystalline 3-O-fucosyllactose of claim 1, wherein the 3-O-fucosyllactose displays, in DSC investigations, an endothermic reaction with peak temperature at 243±3° C.

9. The crystalline 3-O-fucosyllactose of claim 1, wherein the 3-O-fucosyllactose displays, in DSC investigations, an endothermic reaction with peak temperature at 243±2° C.

10. The crystalline 3-O-fucosyllactose of claim 1, wherein the crystalline 3-O-fucosyllactose displays, in DSC investigations, an endothermic reaction with peak temperature at 243±1° C.

11. A pharmaceutical composition comprising the crystalline 3-O-fucosyllactose of claim 1 and a pharmaceutically acceptable carrier.

12. A nutritional formulation comprising the crystalline 3-O-fucosyllactose of claim 1.

13. The nutritional formulation of claim 12, wherein the nutritional formulation is an infant formula.

14. The nutritional formulation of claim 12, wherein the nutritional formulation is a food supplement.

15. A method for producing the crystalline 3-O-fucosyllactose of claim 1, wherein a syrupy 3-O-fucosyllactose is kept under a vacuum of 30 mbar or less.

16. A method for producing crystalline 3-O-fucosyllactose of claim 1, wherein amorphous 3-O-fucosyllactose is suspended in an antisolvent and stirred.

17. A method for producing crystalline 3-O-fucosyllactose of claim 1, wherein crystallization is carried out from a solvent or solvent system in the presence of seed crystals.

* * * * *